United States Patent
Gross (10) Patent No.: US 9,439,724 B2
(45) Date of Patent: Sep. 13, 2016

(54) RESONATING RADIO FREQUENCY ABLATION DEVICE

(71) Applicant: Cook Medical Technologies LLC, Bloomington, IN (US)

(72) Inventor: David C. Gross, Westerville, OH (US)

(73) Assignee: Cook Medical Technologies LLC, Bloomington, IN (US)

( * ) Notice: Subject to any disclaimer, the term of this patent is extended or adjusted under 35 U.S.C. 154(b) by 331 days.

(21) Appl. No.: 14/100,993

(22) Filed: Dec. 9, 2013

(65) Prior Publication Data

US 2014/0171933 A1  Jun. 19, 2014

Related U.S. Application Data

(60) Provisional application No. 61/736,873, filed on Dec. 13, 2012.

(51) Int. Cl.
| | |
|---|---|
| *A61B 18/14* | (2006.01) |
| *A61B 18/08* | (2006.01) |
| *A61B 18/00* | (2006.01) |

(52) U.S. Cl.
CPC ......... *A61B 18/1492* (2013.01); *A61B 18/082* (2013.01); *A61B 2018/00011* (2013.01); *A61B 2018/00023* (2013.01); *A61B 2018/00791* (2013.01); *A61B 2018/1475* (2013.01)

(58) Field of Classification Search
CPC ............ A61B 18/1492; A61B 18/082; A61B 2018/00011; A61B 2018/00791; A61B 2018/00023; A61B 2018/1475
See application file for complete search history.

(56) References Cited

U.S. PATENT DOCUMENTS

| | | | |
|---|---|---|---|
| 1,807,105 A | 5/1931 | Schliephake | |
| 5,271,400 A | 12/1993 | Dumoulin et al. | |
| 5,323,778 A * | 6/1994 | Kandarpa | A61F 7/00 600/411 |
| 6,246,896 B1 | 6/2001 | Dumoulin et al. | |
| 6,272,370 B1 | 8/2001 | Gillies et al. | |
| 6,393,314 B1 * | 5/2002 | Watkins | A61B 5/06 600/411 |
| 6,478,793 B1 | 11/2002 | Cosman et al. | |
| 6,881,214 B2 | 4/2005 | Cosman et al. | |
| 7,848,788 B2 * | 12/2010 | Tulley | G01R 33/34053 324/318 |
| 8,131,339 B2 | 3/2012 | Bonn | |
| 8,187,252 B2 | 5/2012 | Buckley et al. | |
| 2005/0065501 A1 | 3/2005 | Wallace | |
| 2011/0015713 A1 | 1/2011 | Min | |
| 2011/0202117 A1 | 8/2011 | Marshall et al. | |
| 2011/0301450 A1 * | 12/2011 | Hue | A61B 18/14 600/411 |

OTHER PUBLICATIONS

Amjad, A. "Specific Absorption Rate During Magnetic Resonance Imaging," *Dissertation Submitted to the Faculty of Purdue University*, West Lafayette, IN, 2007, 185 pages.

(Continued)

*Primary Examiner* — Michael Peffley
(74) *Attorney, Agent, or Firm* — Brinks Gilson & Lione (57) ABSTRACT

The invention relates to methods, systems, and devices for ablating a tumor with heat delivered from a non-ferrous metallic rod having a length adapted to support resonating radio frequency waves along the longitudinal axis of the rod. The tumor ablation may be carried out in an MRI where the radio frequency transmitter of the MRI wirelessly delivers the energy to heat the metallic rod.

20 Claims, 3 Drawing Sheets

(56) References Cited

OTHER PUBLICATIONS

Armenean, C.; Perrin, E.; Armenean, M.; Beuf, O.; Pilleul, F.; Saint-Jalmes, H. "RF-Induced Temperature Elevation Along Metallic Wires in Clinical Magnetic Resonance Imaging: Influence of Diameter and Length," *Magn. Res. Med.*, 2004, 52, 1200-1206.

Bassen, H.; Kam, A.; Kainz, W.; Mendoza, G.; Wang, H. "Real Time Measurement of Heating Near Metallic Implants Trhoughout a Phantom Using Phase-Shift MR Thermometry," *Proc. Intl. Soc. Mag. Reson. Med.*, 2006, 14, 698.

Bennett, L.H.; Wang, P.S.; Donahue, M.J. "Artifacts in Magnetic Resonance Imaging from Metals," *J. Appl. Phys.*, 1996, 79, 6pgs.

Friedman, M.; Mikityansky, I.; Kam, A.; Libutti, S.K.; Walther, M.M.; Neeman, Z.; Locklin, J.K.; Wood, B.J. "Radiofrequency Ablation of Cancer," *Cardiovasc Intervent Radiol.*, 2004, 27, 427-434.

Goldberg, S.N.; Gazelle, G.S.; Mueller, P.R. "Thermal Ablation Therapy for Focal Malignancy: A Unified Approach to Underlying Principles, Techniques, and Diagnostic Imaging Guidance," *AJR*, 2000, 174, 323-331.

Haemmerich, D.; Staelin, S.T.; Tsai, J.Z.; Tungjitkusolmun, S.; Mahvi, D.M.; Webster, J.G. "In vivo Electrical Conductivity of Hepatic Tumours,"*Physiol. Meas.*, 2003, 24, 251-260.

Hug, J.; Nagel, E.; Bornstedt, A.; Schnackenburg, B.; Oswald, H.; Fleck E. "Coronary Arterial Stents: Safety and Artifacts During MR Imaging," *Raidiology*, 2000, 216, 781-787.

Jallal, J. "A Standard Implant for Determination of RF-Induced Local SAR in MRI Heating Tests," *Thesis Submitted to the Faculty of Purdue University*, West Lafayette, IN, 2010, 55 pages.

Konings, M.K.; Bakker, C.J.G. "Intolerable Heating by Resonating RF Waves Around Guidewires," *Dept. Rad., Image. Sci. Inst.*, University Hospital Utrecht, The Netherlands, 1999, 1 page.

Konings, M.K.; Bartels, L.W.; Smits, H.F.M.; Bakker, C.J.G. "Heating Around Intravascular Guidewires by Resonating RF Waves," *J. Mag. Res. Imag.*, 2000, 12, 79-85.

Ladd, M.E.; Quick, H.H.; Boesiger, P.; McKinnon, G.C. "RF Heating of Actively Visualized Catheters and Guidewires," http://cds.ismrm.org/ismrm-1998/PDF2/P0473.PDF, 1998, 1 page.

Leewood, A.; Gross, D.; Crompton, J.; Yushanov, S.; Simonetti, O.; Ding, Y. "Poster Titled: Transient RF Heating of a Passive Implant: Coupled Electromagnetic/Thermal Simulation and Experimental Validation," *ISMRM Workshop on MR Safety in Practice: Now & in the Future*, Lund, Sweden, 2012, 1 page.

Mattel, E.; Triventi, M.; Calcagnini, G.; Censi, F.; Kainz, W.; Mendoza, G.; Bassen, H.I.; Bartolini, P. "Complexity of MRI Induced Heating on Metallic Leads: Experimental Measurements of 374 Configurations," http://www.biomedical-engineering-online.com/content/7/1/11, 2012, 17 pages.

Miklavcic, D.; Payselj, N.; Hart, F.X. "Electric Properties of Tissues," *Wiley Encycl. Biomed. Eng.*, 2006, 1-12.

Miklavcic, D.; Semrov, D.; Valencic, V.; Sersa, G.; Vodovnik, L. "Tumor Treatment by Direct Electric Current: Computation of Electric Current and Power Density Distribution," *Electro. Magnetobiology*, 1997, 16, 119-128.

Nyenhuis, J.A.; Park, S-M.; Kamondetdacha, R.; Amjad, A.; Shellock, F.G.; Rezai, A.R. "MRI and Implanted Medical Devices: Basic Interactions With an Emphasis on Heating," *IEE Trans. Dev. Mat. Rel.*, 2005, 5, 467-480.

O'Rourke, A.P.; Haemmerich, D.; Prakash, P.; Converse, M.C.; Mahvi, D.M.; Webster, J.G. "Current Status of Liver Tumor Ablation Devices," *Expert. Rev. Med. Dev.*, 2007, 4, 523-537.

Park, S.M.; Kamondetdacha, R.; Amjad, A.; Nyenhuis, J.A. "MRI Safety: RF-Induced Heating Near Straight Wires," *IEEE Trans. Mag.*, 2005, 41, 4197-4199.

Qiu, B.; Yeung, C.J.; Du, X.; Atalar, E.; Yang, X. "Development of an Intravascular Heating Source Using an MR Imaging Guidewire," *J. Magn. Res. Imaging*, 2002, 16, 716-720.

Shellock, F.G. "Radiofrequency Energy-Induced Heating During MR Procedures: A Review," *J Magn. Res. Imaging*, 2000, 12, 30-36.

Shellock, F.G.; Forder, J.R. "Drug Eluting Coronary Stent: in vitro Evaluation of Magnet Resonance Safety at 3 Tesla," *J. Cardiov. Magn. Res.*, 2005, 7, 415-419.

Shellock, F.G.; Shellock, V.J. "Metallic Stents: Evaluation of MR Imaging Safety," *AJR*, 1999, 173, 543-547.

Smith, C.D.; Kildishev, A.V.; Nyenhuis, J.A.; Foster, K.S.; Bourland, J.D. "Interactions of Magnetic Resonance Imaging Radio Frequency Magnetic Fields with Elongated Medical Implants," *J. Appl. Phys.*, 2000, 87, 6188-6190.

Todd, N.; Payne, A.; Parker, D. "3-D MR Temperature Imaging with Model Predictive Filtering Reconstruction," *Proc. Intl. Soc. Mag. Reson. Med.*, 2009, 17, 446.

Tungitkusolmun, S.; Staelin, S.T.; Haemmerich, D.; Tsai, J-Z.; Cao, H.; Webster, J.G.; Lee, Jr., F.T.; Mahvi, D.M.; Vorperian, V.R. "Three-Dimensional Finite-Element Analyses for Radio-Frequency Hepatic Tumor Ablation," *IEEE Trans. Biomed. Engin.*, 2002, 49, 3-9.

Yeung, C.J.; Susil, R.C.; Atalar, E. "RF Heating Due to Conductive Wires During MRI Depends on the Phase Distribution of the Transmit Field," *Magn. Res. Med.*, 2002, 48, 1096-1098.

Yeung, C.J.; Susil, R.C.; Atalar, E. "RF Safety of Wires in Interventional MRI: Using a Safety Index," *Magn. Res. Med.*, 2002, 47, 187-193.

\* cited by examiner

RESONATING RADIO FREQUENCY ABLATION DEVICE

RELATED APPLICATIONS

The present patent document claims the benefit of the filing date under 35 U.S.C. §119(e) of Provisional U.S. Patent Application Ser. No. 61/736,873, filed Dec. 13, 2012, which is hereby incorporated by reference.

TECHNICAL FIELD

The present invention relates to devices, systems, and methods which use radio frequency waves to resonate electrically conductive materials in dielectric mediums in order to generate heat sufficient to ablate tumor tissue. The invention can be used inside a magnetic resonance imager (MRI) where energy received from the radio frequency (RF) coil supplies the heat to ablate the tumor tissue.

BACKGROUND OF THE INVENTION

RF ablation is used in multiple applications to treat numerous diseases. Traditionally, RF ablation has been applied to heart tissue to treat cardiac arrhythmia (e.g., atrial fibrillation) by destroying abnormal heart tissue. This procedure is performed on thousands of patients annually around the world and is becoming more widely accepted as an increasing number of reports show safety and efficacy. Reported success rates for catheter ablation therapy for cardiac arrhythmias exceed 95% for RF ablation of most accessory pathways and AV nodal reentry. RF ablation is also well known for treating tumors in the liver as well as the lung, breast, pancreas, bile duct, bone, and kidney. Additionally, RF ablation has been used to treat varicose veins, uterine fibroids, and as a method for pain management. RF ablation is the most commonly used minimally invasive therapy in the United States to treat hepatocellular carcinoma (HCC) and liver metastases. Percutaneous RF ablation therapy has been shown to be a cost-effective treatment when compared to palliative care for malignant hepatic neoplasms.

Current RF ablation devices require electrodes to be hard wired to an RF generator. These electrodes can then be delivered into the patient percutaneously. Then the RF generator is used to adjust the power (and thus the temperature) that the electrode delivers to the tissue of interest. MRI is a rapidly growing imaging technique and it is beginning to be used intraoperatively. MRI provides a high soft-tissue contrast which allows physicians to delineate tumor tissue and the surrounding anatomy much better than ultrasonography and computed tomography. MRI is sensitive to thermal effects which allows for monitoring of the RF ablation, commonly referred to as real time thermography. While MRI does not emit ionizing radiation, it does pose safety risks concerning magnetically induced displacement force. This concern increases when the MR system is used intraoperatively causing MR unsafe objects to be in the room close to the MR system, such as an RF generator.

Thus, there is a need for improved techniques that permit RF ablation in an MRI without the difficulties of using an external RF generator or other potentially hazardous equipment.

SUMMARY OF THE INVENTION

The present invention relates to methods, systems, and devices for tumor ablation by wirelessly harnessing the energy from an RF generator to heat a non-ferrous metallic rod by resonating RF waves.

One aspect of the invention provides a non-ferrous metallic rod adapted to wirelessly receive radio frequency energy from a radio frequency generator of a magnetic resonance imager where the non-ferrous metallic rod has a distal tip, a longitudinal axis, and a resonant length for the magnetic resonance imager (i.e., a length suitable for resonating radio frequency waves to travel along the longitudinal axis). The distal tip of the rod is configured to heat a tumor. In one embodiment, the non-ferrous metallic rod is surrounded by an external housing except for the distal tip, which projects beyond the distal opening of the housing, where the distal end of the housing is adapted to sealingly engage the outer surface of the rod. In one embodiment, the housing contains a lossy medium with electrical conductivity of about 0.1 to about 0.7 siemens per meter. In another embodiment, the housing is further equipped with a cooling connection to provide a cooling fluid to the interior of the housing.

Another aspect of the invention provides a method of ablating a tumor with a resonating radio frequency ablation device. One embodiment provides a method of ablating a tumor by providing a resonating radio frequency ablation device having a resonant length non-ferrous metallic rod, advancing a patient into a bore of a magnetic resonance imager, advancing the distal tip of the resonating radio frequency ablation device to an operative position at a tumor treatment site within the patient, orienting the resonating radio frequency ablation device in the magnetic resonance imager to interact with radio frequency waves from the magnetic resonance imager, and supplying radio frequency energy from the magnetic resonance imager to the resonating radio frequency ablation device sufficient to heat the distal tip of the non-ferrous metallic rod.

Yet another aspect of the invention provides a system for ablating a tumor comprising a resonating radio frequency ablation device, a radio frequency generator, and an imaging system.

DETAILED DESCRIPTION

RF energy incident upon a conducting metallic wire-like object can produce resonance RF waves along the object. Incident RF waves can reflect back from the end-points of a wire-like structure of appropriate length to form standing RF waves which can produce significant heating at the ends of the wire-like structure. The resonance phenomenon has been investigated from the standpoint of patient safety in the use of metallic guidewires or elongated medical implants during MRI procedures.

The resonating radio frequency ablation device of the invention wirelessly harnesses the energy from an RF generator to heat a non-ferrous metallic rod by resonating RF waves. In general, the length of the rod is suitable for resonating radio frequency waves to travel along the longitudinal axis of the rod. The resonant length of the non-ferrous metallic rod is determined by the incident radio frequency waves and the environment surrounding the rod. The theoretical resonant length is equal to the half-wavelength of the incident radio frequency energy, where the wavelength λ can be calculated from the following equation:

$$\lambda = \frac{2\pi}{\omega\sqrt{\frac{\mu\varepsilon}{2}}\sqrt{1+\left(1+\frac{\sigma^2}{\omega^2\varepsilon^2}\right)^{\frac{1}{2}}}}$$

where ω is the angular frequency (i.e., ω=2πf, where f is frequency in Hz), μ is magnetic permeability of the medium surrounding the rod (H/m), ∈ is the permittivity of the medium surrounding the rod (i.e., ∈=∈$_r$∈$_o$, where ∈$_r$ is relative permittivity of the medium and ∈$_o$ is permittivity in a vacuum), and σ is the electrical conductivity of the medium surrounding the rod (S/m). Increasing the electrical conductivity of the medium decreases the resonant length, whereas adding a layer of insulation or decreasing the permittivity of the insulation increases the resonant length.

A typical MRI system includes a static magnetic field generator, a pulsed time-varying gradient field generator, and an RF transmitter for generating pulsed RF waves. The RF transmitter of an MRI emits pulses of RF energy that interact with the non-ferrous metallic rod. The frequency of the RF energy is related to the strength of the static magnetic field of the MRI. A 1.5 T MRI provides a RF pulse of 64 MHz, whereas a 3.0 T MRI provides a RF pulse of 128 MHz. Thus, where the incident RF waves originate with the RF generator of a magnetic resonance imager, the wavelength of the RF energy will relate to magnetic strength.

The "resonant length" of the non-ferrous metallic rod of the invention refers to a range of lengths around the theoretical resonant length that provide substantial heating in a particular surrounding medium. Lengths significantly greater than or less than the resonant length produce less heating at the end of the rod. However, the resonant length encompasses the theoretical resonant length as well as lengths immediately above and below the theoretical resonant length since substantially the same degree of heating is provided by this range of lengths. For example, the resonant length may be about 80% to about 120% of the theoretical resonant length.

In a medium of electrical conductivity of about 0.5 S/m, the theoretical resonant length of an uninsulated metallic rod in a 3.0 T MRI is about 10 cm, and about 20 cm in a 1.5 T MRI. The resonant length will thus vary with the frequency of the RF energy and hence the magnetic field strength. In a medium of electrical conductivity of about 0.5 S/m, the resonant length of an uninsulated non-ferrous metallic rod in a 1.5 T MRI can vary from about 18 to about 22 cm. Likewise, in a similar environment, the resonant length in a 3.0 T MRI can vary from about 8 to about 12 cm. As explained above, insulating the wire will increase the resonant length, with greater resonant lengths for thicker insulation. On the other hand, increasing the permittivity of the insulation decreases the resonant length. The length of the rod may thus be varied as appropriate depending on the particular ablation procedure to be performed, the surrounding medium, and the presence or absence of insulation.

Human tissues display a range of conductivities: about 0.035-0.037 S/m for fat; about 0.059 to about 0.067 S/m for bone; about 0.45 to about 0.5 S/m for liver; and about 1.59 to about 1.69 S/m for intestine. The electrical conductivities of tumors can also vary.

The amount of energy transferred to the non-ferrous metallic rod by the RF energy can be characterized by a Specific Absorption Rate (SAR). An MRI may operate in different modes delivering RF energy, and creating electric fields with whole body averages ranging from 0 to 4 watts/kilogram (W/kg) to human tissue. Relative to background tissue heating, the SAR gain at the tip of a metallic rod increases to an extent depending partly on the proportions of the rod. For example, a smaller diameter rod leads to greater heating at the resonant length. The amount of heating of the non-ferrous metallic rod also varies with the strength of the incident radio frequency waves. In an MRI, the electric field is lower in the center of the bore of the MRI and increases away from the center of the bore of the MRI. Thus, for a comparably proportioned metallic rod, positioning the rod away from the center of the bore will result in greater heating of the rod. Greater heating also occurs when the rod is parallel to the incident electric field with less heating at other angles. The SAR can be calculated from the following equation:

$$SAR = \frac{\sigma|E|^2}{2\rho}$$

where σ is the electrical conductivity of surrounding medium (in S/m), ρ is the mass density of the medium (in kg/m3), and E is the electric field. Using the SAR, the heating profile near the tip of the rod can be calculated from the bioheat equation given here:

$$\rho C_p \frac{\partial T}{\partial t} = K\nabla^2 T + \rho(SAR) - b(T - T_b)$$

where T is temperature (in ° C.) at time t, $C_p$ is the specific heat (in J/kg·° C.), K is the thermal conductivity (in W/m·° C.), b is a constant related to blood flow, and $T_b$ is the blood temperature.

Figure 1:
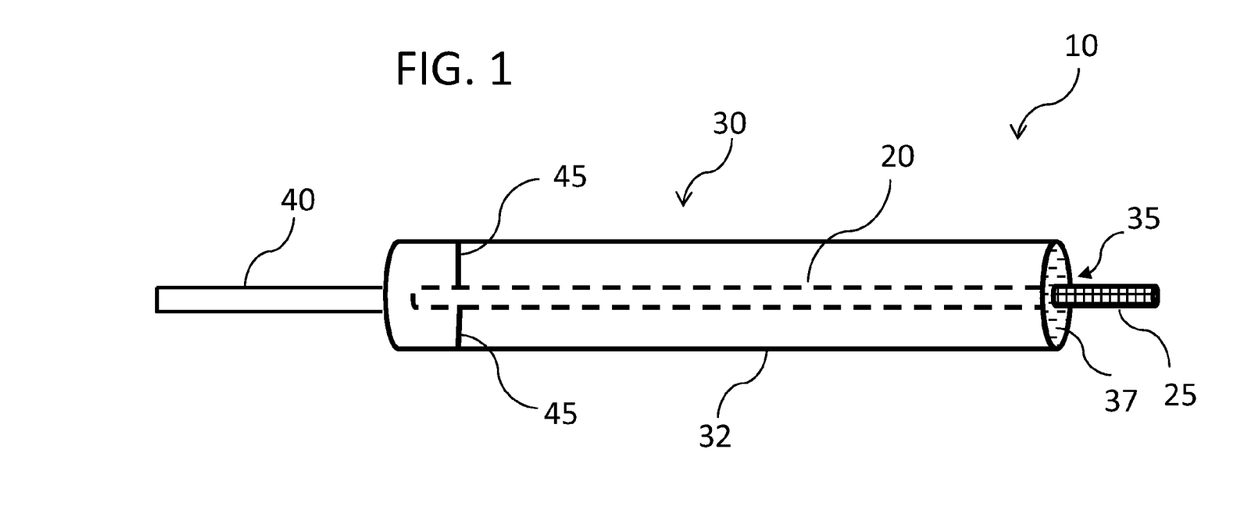
FIG. 1 is a perspective view of one embodiment of the resonating RF ablation device of the invention where the distal tip of the rod has a blunt end.

Referring to FIG. 1, an illustration of one embodiment of the resonating RF ablation device 10 is shown. The non-ferrous metallic rod 20 is positioned within a housing 30 where the distal tip 25 projects past the distal end 37 of the housing through the distal opening 35 of the housing. The distal end of the housing 37 forms a seal around the exterior surface of the metallic rod 20. The distal end 37 may be integral with the body 32 of the housing or it may comprise a separate sealing structure. A handle 40 is optionally present on the proximal end of the housing. In the interior of the housing 30, the rod 20 is spaced from the inner walls of the body of the housing by brackets 45. The distal tip 25, shown in FIG. 1 as a flat-ended tubular structure, may be conical, trocar, beveled, rounded, bent, hook-shaped, angled, or other shape depending on the particular application.

The diameter of the metallic rod 20 depends on the specific treatment and the desired amount of heating at the distal tip 25. The metallic rod 20 may be a fraction of a millimeter to several millimeters in diameter and may have a variety of cross-sectional shapes such as round, square, triangular, etc. In general, decreasing the diameter of the rod 20 increases the amount of heating at the distal tip 25 of the rod.

The metallic rod is made of a metal or combination of metals (i.e., alloys) such as, for example, titanium, copper, nickel, gold, silver, aluminum, alloys, brass, bronze, or nitinol.

The space surrounding the rod 20 within the body 32 of the housing may include a lossy medium with electrical conductivity of about 0.1 to about 0.7 S/m. The length of the rod and the electrical conductivity of the lossy medium are adjusted relative to one another in order that the rod 20 has a resonant length for the particular radio frequency incident on the rod. The electrical conductivity of the lossy medium surrounding the rod may or may not match that of the target tumor. In general, a surrounding lossy medium with electrical conductivity from about 0.1 to about 0.7 S/m are suitable for a resonant length non-ferrous metallic rod to heat sufficiently to ablate a tumor.

Figure 2:
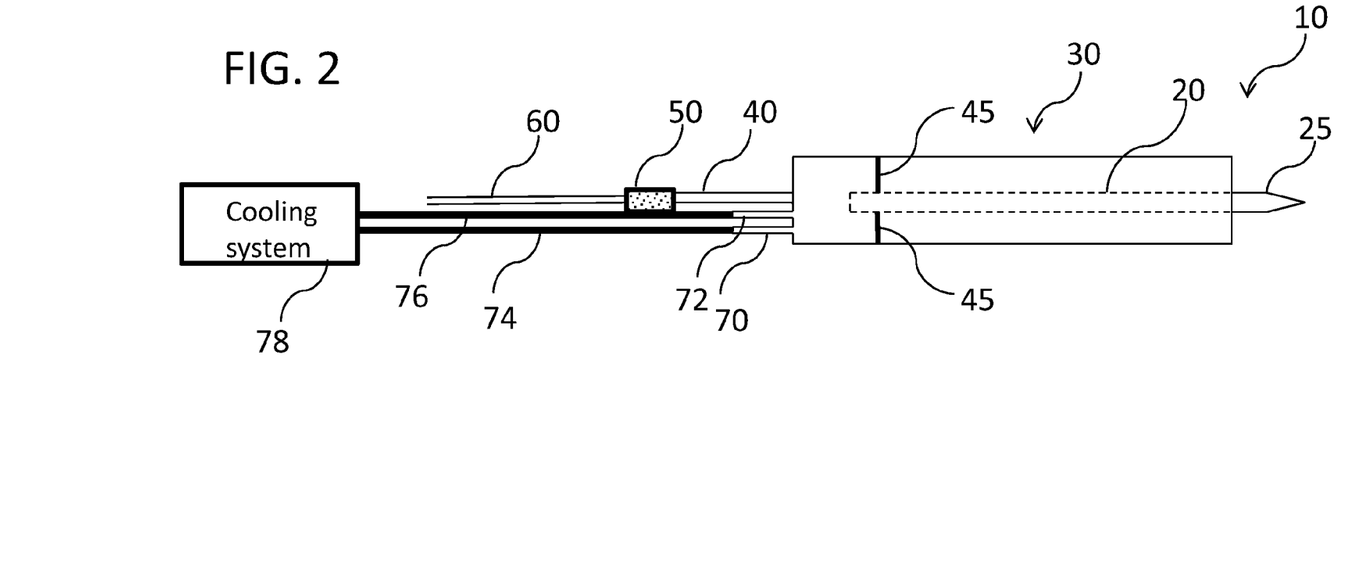
FIG. 2 is a side view of one embodiment of the resonating RF ablation device of the invention where the distal tip of the rod has a conical shape.

In another embodiment shown in FIG. 2, the housing 30 has optional cooling connections 70 and 72 for input and output of cooling fluid. Cooling lines 74 and 76 are connected to cooling connections 70 and 72 to supply a cooling fluid from cooling system 78 into the space surrounding the rod 20 within the housing body 32. The cooling fluid allows one to moderate the temperature of the rod to prevent overheating and charring of tissue. Also illustrated in the embodiment in FIG. 2 are a connector 50 and a pusher 60. The connector 50 joins the handle 40 with the pusher 60. The pusher, in turn, provides a means for advancing the resonating radio frequency ablation device to a tumor treatment site.

Figure 3:
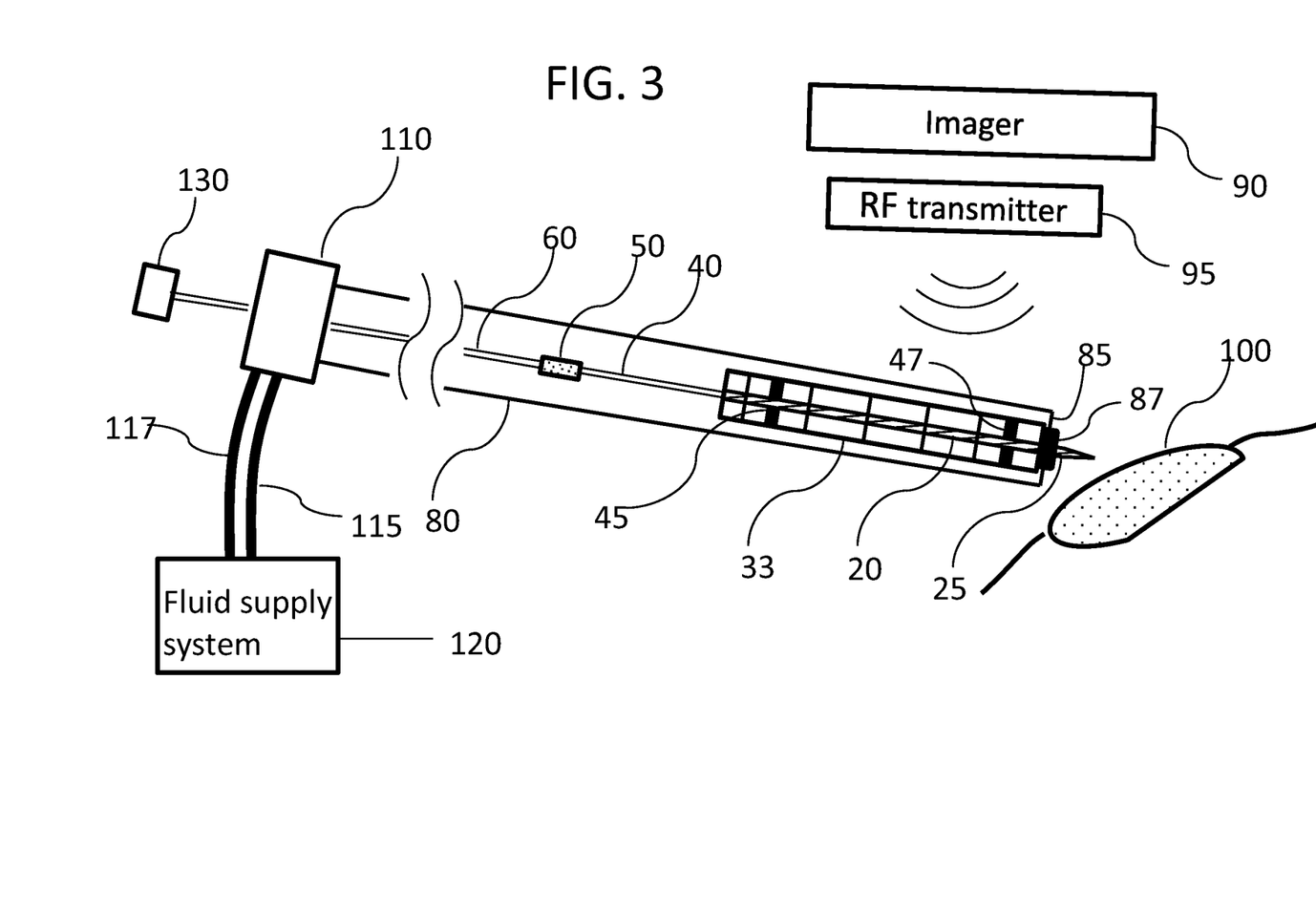
FIG. 3 is a side view of one embodiment of the device, system, and method of the invention where the resonating RF ablation device is advanced to a tumor treatment site through the lumen of a catheter.

FIG. 3 illustrates another embodiment of the resonating RF ablation device where the device 10 is positioned inside a catheter 80 with the distal tip 25 projecting through the distal end 85 of the catheter 80. The embodiment in FIG. 3 shows the housing body as an open cage 33. In the embodiment in FIG. 3, a lossy medium bathes the interior of the catheter passing through the cage 33 to surround the rod 20. A seal 87 is present at the distal end to surround the rod and prevent leakage of fluid from the distal end. Brackets 45 and 47 space the rod 20 from the cage 33. Alternatively, the brackets are omitted and the cage 33 is itself adapted to hold the rod in an operative position. As in FIG. 2, the connector 50 joins the handle 40 with the pusher 60. The pusher, in turn, provides a means for advancing the resonating radio frequency ablation device to a tumor treatment site. The pusher 60 may be operated at the proximal end of the catheter using pusher handle 130, connected through the hub 110. The lossy medium inside the catheter may also be cooled to control heating of the rod. The lossy medium may be supplied to the interior of the catheter from a fluid supply system 120 located at the proximal end of the catheter. Fluid may be supplied to and from the catheter by fluid supply lines 115 and 117 through hub 110.

In operation, a guiding catheter 80 may be first positioned proximate a tumor 100 and the device 10 advanced through the guiding catheter to the tumor 100. The distal end 85 and the distal tip 25 are adapted to allow the distal tip 25 to project through the distal end 85 of the catheter, which forms a seal around the rod 20. Alternatively, a separate seal 87 may be provided. The interior of the catheter is supplied with a lossy medium to surround and bathe the surface of the rod 20. The catheter may be advanced to the tumor site with the use of imager 90. The distal tip 25 is positioned at an operative distance proximate a tumor where the rod 20 receives radiofrequency energy from an RF transmitter such as 95. The rod 20 has a resonant length that supports resonating RF waves along the rod in the lossy medium surrounding the rod 20. The RF energy causes the device to resonate and the electric field scatters off the distal tip 25, thereby causing an increase in temperature in the tumor thereby ablating the tumor. An "operative position" or an "operative distance" refers to a positioning of the distal tip at a sufficient proximity to a tumor such that heat from the distal tip can ablate tumor tissue. An "operative position" thus encompasses positions wherein the distal tip may or may not be in physical contact with a tumor.

MRI may be used to guide the catheter 80 and rod 20 allowing the entire operation to be performed in an intraoperative MR suite. Once the guiding catheter 80 is appropriately positioned with the use of MRI, the metallic rod 20 can be advanced through the guiding catheter to the appropriate position either with or without the use of MR imaging. Once the distal tip 25 is operatively positioned, the MR imaging can be initiated, causing the metallic rod 20 to resonate from the oscillating electromagnetic field and heat the distal tip 25.

MRI systems also have sensing and imaging components. MRI thermography may be used to monitor the temperature of the distal tip 25 and the surrounding tissue. The isotherm regions created by heating and ablation may be visualized with the imager to determine the extent of tissue ablation. Alternatively, the metallic rod may be periodically removed to monitor the temperature of the tissue via MRI thermography. Alternatively, if so desired, a temperature sensor may optionally be included at the distal tip of the rod to monitor the increase in temperature.

At a temperature of about 46° C. for about 1 hour, irreversible damage occurs to living cells. Above 43° C., the time required to cause cell death is halved with each degree centigrade increase in temperature. Most mammalian cells do not survive at temperatures exceeding 49° C. for an extended period of time. At about 50-52° C., cell death occurs in about 4-6 minutes. At temperatures from about 60° C. to about 100° C., cell death is essentially instantaneous. At temperatures above 105° C., vaporization and charring of tissue occurs, thereby reducing the effectiveness of continued ablation therapy as the charred tissue creates an electrically isolating layer. By using an appropriate resonant length rod 20, appropriate positioning within the bore of the MR system, and high power MR scanning parameters, temperatures of 60° C. can be obtained with the resonating RF ablation device, for example, by operating an MRI so as to deliver RF energy with a whole body average of about 4 W/kg.

The invention may be used to ablate a range of tumor types such as, for example, lung tumors, hepatocellular carcinoma, bone tumors, breast tumors, pancreas tumors, bile duct tumors, renal and retroperitoneal tumors, osteoid osteomas, colorectal cancer, hepatic and cerebral metastases.

Radio frequency ablation may be performed with percutaneous, laparoscopic, or open-surgical approaches. The choice depends on the condition of the patient, tumor size, number, location, or growth pattern. The resonating RF ablation device may be placed through the skin and into the tumor with imaging guidance. Percutaneous ablation may be monitored by real-time ultrasound imaging, computed tomography, or magnetic resonance imaging.

One advantage of the resonating RF ablation device of the invention is that it may function with essentially no circuitry. For example, there is no need for a grounding pad to complete an electrical circuit or for an RF generator. This reduces the safety risks of having multiple MR unsafe objects in the room (e.g., an RF generator), thereby increasing the simplicity of the ablation procedure. By eliminating the need for the RF generator and the accompanying equipment, the cost of the procedure could be reduced and the procedure could be performed with greater accuracy in an MR suite.

One aspect of the invention provides a method of ablating a tumor inside a bore of a magnetic resonance imager with a resonating RF ablation device.

In one embodiment of the foregoing method of ablating a tumor, a resonating RF ablation device is first provided where the resonating RF ablation device includes a non-ferrous metallic rod adapted to wirelessly interact with radio frequency energy from a radio frequency transmitter of a magnetic resonance imager, the non-ferrous metallic rod having a distal tip, a longitudinal axis, and a resonant length for the magnetic resonance imager, the distal tip being configured to heat a tumor. A patient is advanced into the bore of a MRI and the distal tip of the resonating radio frequency ablation device is advanced to an operative position at a tumor treatment site within the patient. The resonating RF ablation device is oriented in the MRI to interact with radio frequency waves from the MRI and sufficient radio frequency energy is supplied from the MRI to the resonating RF ablation device to heat the distal tip 25, thereby ablating the tumor tissue. The steps of advancing the patient or the resonating RF ablation device, the step of orienting the ablation device, and the step of supplying radio frequency energy may be performed in any order.

In a further embodiment of the foregoing method of ablating a tumor, the resonating RF ablation device further includes a housing, where the housing has a distal end and a distal opening where the non-ferrous metallic rod is positioned within the housing with the distal tip projecting through the distal opening of the housing, wherein the distal end of the housing or a separate seal is adapted to sealingly engage the non-ferrous metallic rod, the housing containing a lossy medium with electrical conductivity of about 0.1 to about 0.7 siemens per meter. In another embodiment, the lossy medium has a conductivity of about 0.4 to about 0.6 siemens per meter. In yet another embodiment, the lossy medium has a conductivity of about 0.5 siemens per meter (e.g., about 0.46 to about 0.54 S/m).

In a further embodiment of the foregoing method of ablating a tumor, the resonating radio frequency ablation device is advanced to an operative position at a tumor treatment site by positioning a catheter adjacent the tumor treatment site and advancing the resonating radio frequency ablation device through the catheter until the distal tip of the resonating radio frequency ablation device reaches the operative position at the tumor treatment site. In another embodiment, the resonating radio frequency ablation device advanced through the catheter includes a housing as described hereinabove.

In a further embodiment of the foregoing method of ablating a tumor, a magnetic resonance imager is used to guide positioning of the catheter used to advance the distal tip of the resonating radio frequency ablation device to the tumor treatment site.

In another embodiment of the foregoing method, the catheter is supplied with a lossy medium with electrical conductivity of about 0.1 to about 0.7 siemens per meter to surround and bathe the surface of the non-ferrous metallic rod. In another embodiment, the lossy medium has a conductivity of about 0.4 to about 0.6 siemens per meter. In yet another embodiment, the lossy medium has a conductivity of about 0.5 siemens per meter (e.g., about 0.46 to 0.54 S/m). In another embodiment, the medium supplied to the catheter to surround and bathe the surface of the non-ferrous metallic rod provides cooling to the rod. In another embodiment of the method, the resonating radio frequency ablation device advanced through the catheter includes an open housing—one example of which is shown in FIG. 3—to space the rod from the sides of the catheter.

In yet another embodiment of the foregoing method of ablating a tumor, the catheter used to advance the resonating radio frequency device has a seal at the distal end where the distal tip of the non-ferrous metallic rod is advanced through the seal and into an operative position.

In still another embodiment of the foregoing method of ablating a tumor, sufficient radio frequency energy is supplied to the resonating radio frequency ablation device to heat the distal tip to a temperature sufficient to ablate a tumor. For example, sufficient energy is delivered to heat the distal tip of the rod to about 46° C. to about 100° C. In another embodiment, the distal tip is heated to about 46° C. to about 50° C. In another embodiment, the distal tip is heated to about 50° C. to about 60° C. In another embodiment, the distal tip is heated to about 60° C. to about 100° C. In another embodiment, the distal tip is heated to about 60° C.

Another aspect of the invention provides a system for ablating a tumor comprising a resonating radio frequency ablation device, a radio frequency transmitter, and an imaging system.

One embodiment of the foregoing system for ablating a tumor includes: (1) a resonating RF ablation device, where the resonating RF ablation device includes a non-ferrous metallic rod adapted to wirelessly interact with radio frequency energy from a radio frequency transmitter of a magnetic resonance imager, the non-ferrous metallic rod having a distal tip, a longitudinal axis, and a resonant length for the magnetic resonance imager, the distal tip being configured to heat a tumor; (2) a radio frequency transmitter; and (3) an imaging system.

Another embodiment of the foregoing system for ablating a tumor includes a resonating RF ablation device further including a housing, where the housing has a distal end and a distal opening where the non-ferrous metallic rod is positioned within the housing with the distal tip projecting through the distal opening of the housing, wherein the distal end of the housing is adapted to sealingly engage the non-ferrous metallic rod. Alternatively, a separate seal is provided. The housing contains a lossy medium with electrical conductivity of about 0.1 to about 0.7 siemens per meter. In another embodiment, the lossy medium has a conductivity of about 0.4 to about 0.6 siemens per meter. In yet another embodiment, the lossy medium has a conductivity of about 0.5 siemens per meter (e.g., about 0.46 to 0.54 S/m).

Yet another embodiment of the foregoing system for ablating a tumor further includes a catheter. In still another embodiment, the catheter contains a lossy medium with electrical conductivity of about 0.1 to about 0.7 siemens per meter. In another embodiment, the lossy medium has a conductivity of about 0.4 to about 0.6 siemens per meter. In yet another embodiment, the lossy medium has a conductivity of about 0.5 siemens per meter (e.g., about 0.46 to 0.54 S/m). In another embodiment, the catheter has a distal end and a seal at the distal end where the seal is adapted to be punctured by the distal tip of the non-ferrous metallic rod.

In another embodiment of the foregoing system for ablating a tumor, the radio frequency transmitter and the imager are components of a magnetic resonance imager and the non-ferrous metallic rod has a resonant length for the magnetic resonance imager.

In another embodiment of the foregoing system for ablating a tumor, the system includes a cooling system where the resonating radio frequency ablation device further comprises a housing, the housing having a distal end and a distal opening, where the non-ferrous metallic rod is positioned within the housing with the distal tip projecting through the distal opening of the housing, wherein the distal end of the housing is adapted to sealingly engage the non-ferrous metallic rod, and wherein the housing further comprises a cooling connection in communication with the cooling system.

Another embodiment of the foregoing systems includes a temperature sensor adapted to measure the temperature of the distal end of the non-ferrous metallic rod.

EXAMPLE 1

Figure 4:
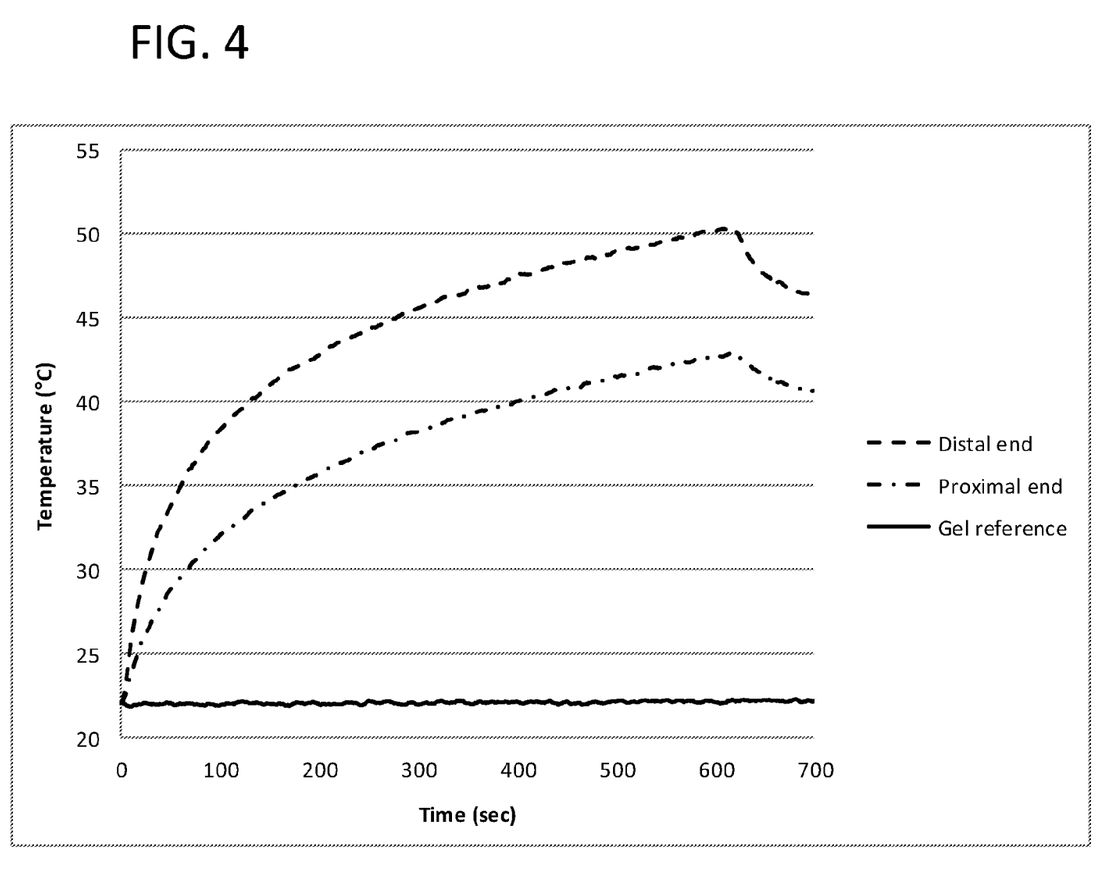
FIG. 4 is a graph showing the temperature increase at the distal and proximal ends for a 10 cm long titanium rod in a 3.0T MRI after 10 minutes of RF energy delivery (Example 1).

The proximal end of a titanium rod measuring 10 cm long and ⅛" in diameter was inserted into the end of an 8 Fr inner diameter catheter. The titanium rod included two 1 mm diameter holes drilled through the rod transverse to the longitudinal axis of the rod. Fluoroptic® temperature probes were inserted into the holes at each end of the titanium rod. The rod, catheter and temperature probes were submersed into a gel within a clear plastic phantom. The titanium rod was positioned 1.5 cm from the wall and bottom of the phantom and centered along the length of the phantom. The gel was made from approximately 50 g of polyacrylic acid, 33 g of NaCl and 25 L of distilled $H_2O$. The purpose of this gel was to approximate the conductivity of human tissue (about 0.47 S/m according to ASTM F2182-11a). The phantom was then placed at isocenter within the bore of the MR system (3.0 T). A scan was performed and the temperature of the electrically passive titanium rod was monitored. The results are shown in FIG. 4. After scanning for 10 minutes, the temperature at the distal tip of the rod increased by 28.39° C. above the room temperature of 22° C., thus reaching a temperature of 50.39° C. As explained above, this temperature is sufficient to ablate tissue over a period of 4-6 minutes. Higher absolute temperatures are expected to be achievable at the distal tip in an in vivo setting where the procedure would start at body temperature (i.e., about 37° C.) rather than 22° C. Higher temperatures are also expected by allowing the MRI to scan for longer periods of time.

The foregoing description of the invention has been presented for purposes of illustration and description, and is not intended to be exhaustive or to limit the invention to the precise form disclosed. The description was selected to best explain the principles of the invention and practical application of these principals to enable others skilled in the art to best utilize the invention in various embodiments and various modifications as are suited to the particular use contemplated.

What is claimed is:

1. A method for ablating a tumor inside a bore of a magnetic resonance imager with a resonating radio frequency ablation device, the resonating radio frequency ablation device comprising (i) a non-ferrous metallic rod adapted to wirelessly interact with radio frequency energy from a radio frequency transmitter of a magnetic resonance imager, the non-ferrous metallic rod having a distal tip, a longitudinal axis, and a resonant length for the magnetic resonance imager, the distal tip being configured to heat a tumor, and (ii) a housing, the housing having a distal end and a distal opening where the non-ferrous metallic rod is positioned within the housing with the distal tip projecting through the distal opening of the housing; wherein a lossy medium with electrical conductivity of about 0.1 to about 0.7 siemens per meter surrounds the non-ferrous metallic rod within the housing, the method comprising the steps of:
   (a) advancing a patient into the bore of the magnetic resonance imager;
   (b) advancing the distal tip of the resonating radio frequency ablation device to an operative position at a tumor treatment site within the patient;
   (c) orienting the resonating radio frequency ablation device in the magnetic resonance imager to interact with radio frequency waves from the radio frequency transmitter; and
   (d) supplying radio frequency energy from the radio frequency transmitter to the resonating radio frequency ablation device sufficient to heat the distal tip of the non-ferrous metallic rod.

2. The method of claim 1, wherein the distal end of the housing is adapted to sealingly engage the non-ferrous metallic rod and the housing contains the lossy medium.

3. The method of claim 1 wherein advancing the distal tip of the resonating radio frequency ablation device to an operative position at a tumor treatment site comprises:
   positioning a catheter adjacent the tumor treatment site and advancing the resonating radio frequency ablation device through the catheter until the distal tip of the resonating radio frequency ablation device reaches the operative position at the tumor treatment site.

4. The method of claim 3 wherein advancing the distal tip of the resonating radio frequency ablation device to an operative position at a tumor treatment site further comprises using the magnetic resonance imager to guide positioning of the catheter.

5. The method of claim 3 wherein the catheter has a distal end and a seal at the distal end, the method further comprising the step of advancing the distal tip of the non-ferrous metallic rod through the seal.

6. The method of claim 1 wherein sufficient radio frequency energy from the magnetic resonance imager is supplied to the resonating radio frequency ablation device to heat the distal tip to about 46° C. to about 100° C.

7. A system for ablating a tumor comprising:
   (a) a resonating radio frequency ablation device comprising (i) a non-ferrous metallic rod adapted to wirelessly interact with radio frequency energy from a radio frequency transmitter, the non-ferrous metallic rod having a distal tip, a longitudinal axis, and a resonant length for the radio frequency transmitter, the distal tip being configured to heat a tumor, and (ii) a housing, the housing having a distal end and a distal opening where the non-ferrous metallic rod is positioned within the housing with the distal tip projecting through the distal opening of the housing; wherein the lossy medium with electrical conductivity of about 0.1 to about 0.7 siemens per meter surrounds the non-ferrous metallic rod within the housing;
   (b) a radio frequency transmitter; and
   (c) an imaging system.

8. The system of claim 7, wherein the distal end of the housing is adapted to sealingly engage the non-ferrous metallic rod and the housing contains the lossy medium.

9. The system of claim 8 further comprising a cooling system wherein the housing further comprises a cooling connection in communication with the cooling system.

10. The system of claim 7 further comprising a catheter, wherein the catheter is adapted to advance the resonating radio frequency ablation device therethrough.

11. The system of claim 10 wherein the catheter contains the lossy medium.

12. The system of claim 10 wherein the catheter has a distal end and a seal at the distal end, the seal being adapted to be punctured by the distal tip of the non-ferrous metallic rod.

13. The system of claim 7 wherein the imager and the radio frequency transmitter are components of a magnetic resonance imager and the non-ferrous metallic rod further has a resonant length for the magnetic resonance imager.

14. The system of claim 7 further comprising a temperature sensor adapted to measure the temperature of the distal end of the non-ferrous metallic rod.

15. A resonating radio frequency ablation device comprising:
 a non-ferrous metallic rod adapted to wirelessly interact with radio frequency energy from a radio frequency transmitter of a magnetic resonance imager, the non-ferrous metallic rod having a distal tip, a longitudinal axis, and a resonant length for the magnetic resonance imager, wherein the distal tip is configured to heat a tumor; and
 a housing, the housing having a distal end and a distal opening, where the non-ferrous metallic rod is substantially surrounded by the housing with the distal tip projecting through the distal opening of the housing, wherein the distal end of the housing is adapted to sealingly engage the non-ferrous metallic rod.

16. The resonating radio frequency ablation device of claim 15 wherein the housing further comprises a cooling connection.

17. The resonating radio frequency ablation device of claim 15 wherein the housing contains a lossy medium with electrical conductivity of about 0.1 to about 0.7 siemens per meter.

18. The resonating radio frequency ablation device of claim 15 wherein the non-ferrous metallic rod is made of titanium.

19. The resonating radio frequency ablation device of claim 15 wherein the resonant length is about 10 or about 20 centimeters.

20. The resonating radio frequency ablation device of claim 15 wherein the resonant length is about 80% to about 120% of a theoretical resonant length.

* * * * *

UNITED STATES PATENT AND TRADEMARK OFFICE
CERTIFICATE OF CORRECTION

| | |
|---|---|
| PATENT NO. | : 9,439,724 B2 |
| APPLICATION NO. | : 14/100993 |
| DATED | : September 13, 2016 |
| INVENTOR(S) | : David C. Gross |

It is certified that error appears in the above-identified patent and that said Letters Patent is hereby corrected as shown below:

In the Claims

In Column 10, Claim 7, Line 55, after "housing; wherein", replace "the" (second occurrence) with --a--.

Signed and Sealed this
Thirteenth Day of March, 2018

Andrei Iancu
*Director of the United States Patent and Trademark Office*